US 6,764,591 B1

(12) United States Patent
Dutta et al.

(10) Patent No.: US 6,764,591 B1
(45) Date of Patent: Jul. 20, 2004

(54) POTENTIOMETRIC SENSORS COMPRISING YTTRIA-STABILIZED ZIRCONIA AND MEASUREMENT METHOD OF TOTAL $NO_X$ SENSING WITHOUT CO INTERFERENCE

(75) Inventors: Prabir K. Dutta, Worthington, OH (US); Nicholas F. Szabo, Columbus, OH (US)

(73) Assignee: The Ohio State University, Columbus, OH (US)

( * ) Notice: Subject to any disclaimer, the term of this patent is extended or adjusted under 35 U.S.C. 154(b) by 113 days.

(21) Appl. No.: 10/061,116

(22) Filed: Feb. 1, 2002

(51) Int. Cl.$^7$ .............................................. G01N 27/407

(52) U.S. Cl. ...................... 205/781; 204/424; 204/409

(58) Field of Search ................................ 204/421–429, 204/409; 205/781

(56) References Cited

U.S. PATENT DOCUMENTS

| | | | | |
|---|---|---|---|---|
| 5,143,696 | A | * 9/1992 | Haas et al. | .................... 422/90 |
| 5,413,691 | A | * 5/1995 | Kaneyasu et al. | |
| 5,705,129 | A | 1/1998 | Takahashi et al. | ............. 422/90 |
| 5,897,759 | A | * 4/1999 | Kurosawa et al. | |
| 5,939,615 | A | * 8/1999 | Kato et al. | |
| 6,062,064 | A | 5/2000 | Yoshida et al. | ............... 73/23.2 |
| 6,468,407 | B2 | * 10/2002 | Clyde et al. | |
| 6,551,497 | B1 | * 4/2003 | Gao et al. | |

OTHER PUBLICATIONS

Miura, N. et al., *High–temperature potentionmetric/amperometric NOx sensors combining stabilized zirconia with mixed–metal oxide electrode*, Sensors and Actuators B, 52 (1998) 169–178.

Miura, N. et al., *Stabilized zirconia–based sensor using oxide electrode for detection of NOx in high–temperature combustion–exhausts*, Solid State Ionics, 86–88 (1996) 1069–1073.

Miura, N. et al., *Mixed Potential Type NOx Sensor Based on Stabilized Zirconia and Oxide Electrode*, J. Electrochem. Soc. 143 (2) (1996) L33–L35.

Lu, G. et al., *Stabilized zirconia–based sensors using WO3 electrode for detection of NO or NO2*, Sensors and Actuators B, 65 (2000) 125–127.

Kurosawa, H. et al., *Stabilized zirconia–based NOx sensor operative at high temperature*, Solid State Ionics, 79 (1995) 338–343.

Brosha, E.L. et al., *CO/HC sensors based on thin films of LaCoO3 and La0.8Sr0.2CoO3–δ metal oxides*, Sensors and Actuators B, 69 (2000) 171–182.

Mukundan, R. et al., *Ceria–Electrolyte–Based Mixed Potential Sensors for the Detection of Hydrocarbons and Carbon Monoxide*, Electrochemical and Solid State Letters, 2(8) (1999) 412–414.

(List continued on next page.)

*Primary Examiner*—Kaj K. Olsen
(74) *Attorney, Agent, or Firm*—Standley Law Group LLP

(57) ABSTRACT

A novel measurement system for determining total $NO_X$, including NO and $NO_2$ concentration without interference from CO, from a gas sample is presented. The measurement system comprises a gas conduit having an upstream end and a downstream end. The gas conduit carries a gas comprising $NO_X$. Disposed within the gas conduit is a catalytic filter comprising platinum and a zeolite. The gas flowing through the gas conduit interacts with the catalytic filter to form an equilibrium mixture of NO and $NO_2$ from the gas comprising $NO_X$. The measurement system further comprises a sensor element comprising an electrolyte substrate upon which are disposed a sensing potentiometric electrode adapted to contact the equilibrium mixture of NO and $NO_2$ and a reference potentiometric electrode. In practice, there should be a temperature difference between the catalytic filter and the sensor element. Also provided is a method of determining the total $NO_X$ content in a gas comprising $NO_X$ based on the measurement system.

21 Claims, 7 Drawing Sheets

OTHER PUBLICATIONS

Munkundan, R. et al., *A Mixed–Potential Sensor Based on a Ce0.8Gd0.2O1.9 Electrolyte and Platinum and Gold Electrodes*, J. Electrochem. Soc. 147 (4) (2000) 1583–1588.

Hibino, T. et al., *Non–Nernstian Behavior at Modified Au Electrodes for Hydrocarbon Gas Sensing*, J. Electrochem. Soc. 146 (9) (1999) 3361–3366.

Walcarius, A., *Zeolite–Modified Electrodes in Electroanalytical Chemistry*, Analytical Chimica Acta, 384, pp. 1–16 (1999).

Walcarius, A., *Factors Affecting the Analytical Applications of Zeolite Modified Electrodes: Indirect Detection of Non-electroactive Cations*, Analytical Chimica Acta, 388, pp. 79–91 (1991).

Fukui, K. et al., *CO Gas Sensor Based on Au–$La_2O_3$ Added $SnO_2$ Ceramics with Siliceous Zeolite Coat*, Sensors and Actuators B, 45, pp. 101–106 (1997).

Tsuchiya, H. et al., *Zeolite Sensor for Nitrogen Monoxide Detection at High Temperature*, Mat. Res. Soc. Symp. Proc., 454, pp. 297–302 (1997).

Enea, O., *Morphological and Electrocatalytic Properties of Gold Deposits on NaY Zeolite*, Electrochim. Acta., pp. 1647 34 (1989).

Osada, M. et al., *Synthesis of a Faujasite Thin Layer and its Application for $SO_2$ Sensing at Elevated Temperatures*, Microporous and Mesoporous Materials, 23, pp. 287–294 (1998).

Liu, B., et al., *A Reagentless Amperometric Biosensor Based on the Coimmobilization of Horseradish Peroidase and Methylene Green in a Modified zeolite Matrix*, Analytica Chimica Acta, 386, pp. 31–39 (1999).

Kunzellman, U. et al., *Biosensor Properties of Glucose Oxidase Immobilized Within $SiO_2$ Gels*, Sensors and Actuators B, 39, pp. 222–228 (1997).

Simon, U. et al., *The effect of $NH_3$ on the Ionic Conductivity of Dehydrated Zeolites Nabeta and Hbeta*, Microporous and Mesoporous Materials, 21, pp. 111–116 1998.

Wolfbeis, O.S., *Novel Oxygen Sensor Material Based on a Ruthenium Bipyridyl Complex Encapsulated in ZeoliteY: Dramatic Differences in the Efficiency of Luminescence Quenching by Oxygen on Going From Surface–Absorbed to Zeolite–Encapsulated Flourophores*, Sensors and Actuators B, 29, pp. 240–245 (1995).

Berger, R. et al., *Micromechanic: A Toolbox for Femtoscale Science: Towards a Laboratory on a Tip*, Microelectronic Engineering, 35, pp. 373–379 (1997).

Scandella, L. et al., *Combination of Single Crystal Zeolites and Microfabrication: Two Applications Toward Zeolite Nanodevices*, Microporous and Mesoporous Materials, 21, pp. 403–409 (1998).

Zhuiykov, S. et al., *Stabilized Zirconia–Based NOx Sensor Using ZnFe2O4 Sensing Electrode*, Electrochemical and Solid–State Letters, 4 (9), H19–H21 (2001).

Ruhland, B. et al., *Gas–kinetic Interactions of Nitrous Oxides with SnO2 Surfaces*, Sensors and Actuators B 50, 85–94 (1998).

Imanaka, N. et al., *Nitrogen Oxides Sensor Based on Silicon Nitride Refractory Ceramics*, Electrochemical and Solid–State Letters, 2 (2), 100–101 (1999).

Zhuiykov, S. et al., *Potentiometric NOx Sensor Based on Stabilized Zirconia and NiCr2O4 Sensing Electrode Operating High Temperatures*, Electrochemistry Communications 3, 97–101 (2001).

Miura, N. et al., *Selective Detection of NO by Using an Amperometric Sensor Based on Stabilized Zirconia and Oxide Electrode*, Solid State Ionics 117, 283–290 (1999).

Sberveglieri, G., et al., *Response to Nitric Oxide of Thin and Thick SnO2 Films Containing Trivalent Additives*, Sensors and Actuators B1, 79–82 (1990).

Baratto, C. et al., *Gold–Catalysed Porous Silicon for NOx Sensing*, Sensors and Actuators B 68, 74–80 (2000).

Fruhberger, B. et al., *Detection and Quantification of Nitric Oxide in Human Breath Using a Semiconducting Oxide Based Chemiresistive Microsensor*, Sensors and Actuators B 76, 226–234 (2001).

Ono, M. et al., *Amperometric Based on NASICON and NO Oxidation Catalysts for Detection of Total NOx in Atmospheric Environment*, Solid State Ionics 136–137, 583–588 (2000).

Fleischer, M. et al., *Selective Gas Detection with High–Temperature Operated Metal Oxides Using Catalytic Filters*, Sensors and Actuators B 69, 205–210 (2000).

Kitsukawa, S. et al., *The Interference Elimination for Gas Sensor by Catalyst Filters*, Sensors and Actuators B 65, 120–121 (2000).

Fukui, K. et al., *CO Gas Sensor Based on Au–La2O3 Added SnO2 Ceramics with Siliceous Zeolite Coat*, Sensors and Actuators B 45, 101–106, (1997).

Hugon, O. et al., *Gas Separation with a Zeolite Filter, Application to the Selectivity Enhancement of Chemical Sensors*, Sensors and Actuators B 67, 235–243 (2000).

Kaneyasu, K. et al., *A Carbon Dioxide Gas Sensor Based on Solid Electrolyte for Air Quality Control*, Sensors and Actuators B66, 56–58 (2000).

Szabo, N. et al., *Microporous zeolite Modified yttria Stabilized Zirconia (YSZ) Sensors for Nitric Oxide (NO) Determination in Harsh Environments*, Sensors and Actuators B 4142, 1–8 (2001).

* cited by examiner

POTENTIOMETRIC SENSORS COMPRISING YTTRIA-STABILIZED ZIRCONIA AND MEASUREMENT METHOD OF TOTAL $NO_x$ SENSING WITHOUT CO INTERFERENCE

The present invention was made with Government support under Grant No. EEC-9523358 awarded by the National Science Foundation. The United States Government may have certain rights to this invention under 35 U.S.C. §200 et seq.

TECHNICAL FIELD OF INVENTION

The present invention relates to total nitrogen oxide ($NO_x$) measurement systems for use in harsh environments. The present invention relates to a nitrogen oxide ($NO_x$) measurement system having a platinum and zeolite based catalyst filter and a sensor element having a potential which varies in response to a $NO_x$ component in a gas being measured.

BACKGROUND OF THE INVENTION

There is a continuing need for high temperature $NO_x$ sensors for combustion environments due to government regulations and negative effects on ecosystems and health. The two main types of sensors that have been tested for $NO_x$ are the solid electrolyte (potentiometric and amperometric) and semiconducting types. One of the main drawbacks of these sensors that has hindered their development is the lack of selectivity between the two main $NO_x$ components of interest, NO and $NO_2$. In combustion environments NO is often the dominant $NO_x$ species with $NO_2$ being present to a lesser amount and it would be ideal to have a selective sensor for each. However, the majority of ceramic sensors cannot distinguish between the two species giving a signal response to both NO and $NO_2$. Typically the signals are in opposite directions, although there are some sensors where the NO and $NO_2$ signal was shown to go in the same direction. Nevertheless because the sensors respond to both gases it would be difficult to determine the level of NO and $NO_2$ in a mixture. The majority of reports do not test mixtures of NO and $NO_2$ together, which is most likely because the signal due to NO+$NO_2$ would be less than that of NO or $NO_2$ tested separately because of cancellation effects. In certain studies of solid electrolyte sensors they have been made to be semi-selective to NO or $NO_2$ by polarizing the sensor electrodes.

Another approach has been to develop systems to detect total $NO_x$, which would be a signal due to the sum of NO+$NO_2$. One of the methods proposed to do this has been to build a two-chamber device out of yttria-stabilized zirconia (YSZ) and in the first chamber to electrochemically oxidize all the incoming $NO_x$ gas to $NO_2$ and then detect the $NO_2$ as a "total $NO_x$" signal in the second chamber. This method and its variations have been extensively represented in the patent literature. A second method to detect total $NO_x$ has been to use a chemical or catalytic filter placed before the sensor to alter the incoming gas. For example, materials used as chemical filters such as Mo converters can convert all the $NO_x$ to NO under certain conditions and $KMnO_4$ was shown to partially oxidize NO to $NO_2$ but the disadvantage is that they are both consumed over time and have to be replaced.

Catalytic filters equilibrate the incoming $NO_x$ to a thermodynamically defined ratio depending on the oxygen content of the gas and the temperature. The advantage of the catalytic filter is that it is not consumed in the reaction. The use of a $NO_x$ equilibration catalytic filter before a sensor has the advantage of simplicity and longer life. A Pt-$SiO_2$/$WO_3$ catalyst layer was used on an amperometric design to equilibrate $NO_x$ to $NO_2$ at 150° C. but the effect of higher temperatures was not investigated. Some other catalytic filter materials that have been tested for $NO_x$ equilibration at various temperatures for possible sensor use are Pt black catalyst, Pt on cordierite, $Mn_3O_4$, $Co_3O_4$ and Pt on $Al_2O_3$.

The use of zeolites as a sensor filter for alcohols has been shown before. The zeolite's own properties can be used to transform the incoming gas or it can be used as a support for an additional catalyst. It has also been shown before that gases such as CO, which is also present in a combustion environment, can interfere with the signal for $NO_x$. Thus to measure an accurate level of $NO_x$ the CO cross-sensitivity must be minimized. Our approach in this study was to develop a system that could detect the total $NO_x$ gas concentration in a background of $O_2$ and $N_2$ at high temperatures with minimal CO interference. We used a nonselective YSZ air reference sensor to detect the $NO_x$ and a $NO_x$ equilibration/CO oxidation filter placed before the sensing electrode composed of a Pt catalyst dispersed onto a zeolite Y support. The sensor and the filter were maintained at different temperatures to provide a driving force for the $NO_x$ equilibration reactions.

SUMMARY OF THE INVENTION

The present invention presents a novel measurement system for determining total $NO_x$ concentration, from a gas sample. Total $NO_x$ includes pure NO, pure $NO_2$ and mixtures thereof. The measurement system comprises a gas conduit having an upstream end and a downstream end. The gas conduit carries a gas comprising $NO_x$. The gas introduced into a measurement system of the present invention typically has concentrations of NO, $NO_2$ and CO in the range of 0 to 1000 ppm. Further, the gas typically contains 2 to 3% oxygen ($O_2$). Disposed within the gas conduit is a catalyst filter comprising platinum and a zeolite. The gas flowing through the gas conduit interacts with the catalyst filter at a particular temperature to form an equilibrium mixture of NO and $NO_2$ from the gas comprising $NO_x$. The measurement system further comprises a sensor element having two electrodes on a solid electrolyte yttria-stabilized zirconia; a sensing potentiometric electrode disposed downstream of the catalytic filter device so as to contact the equilibrium mixture of NO and $NO_2$ and a reference potentiometric electrode. Typically, the reference potential electrode is referenced to air.

It is preferred that the catalyst filter contain between 1 to 5% by mass of platinum. Further, it preferred that zeolite Y be used as the zeolite.

It is preferred that the catalytic filter be placed in the gas conduit so as to maximize exposure of the catalyst filter to the gas stream, thereby better effectuating the equilibrium formation of NO and $NO_2$. Further, it is preferred that the catalyst filter be temperature controlled. Heating of the catalytic filter may be accomplished by any conventional means. By adjusting the temperature of the catalytic filter, the equilibrium concentration of NO and $NO_2$ can be adjusted. It is most preferred that the temperature of the catalytic filter be maintained at a temperature below approximately 700° C., to avoid decomposition of the zeolite.

It is preferred that yttria-stabilized-zirconia be used as the solid electrolyte. It is also preferred that the reference potentiometric electrode is constructed of platinum. It is further preferred that the sensing potentiometric electrode is constructed from platinum, chromium oxide or cobalt oxide. It is preferred that the sensor element be temperature controlled. Temperature control of the sensor element may be accomplished by any conventional means. It is most preferred that the electrolyte, along with the sensing potentiometric electrode and the reference potentiometric electrode are maintained at a temperature above approximately 400° C. and below approximately 600° C. Finally, it is preferred that the temperature of the catalytic filter is maintained at a different temperature than the temperature of the sensor element to improve the magnitude of the signal. The greater the temperature difference between the catalytic filter and the sensor element, the larger the magnitude of the signal. It is most preferred to have at least a 100° C. temperature difference between the catalytic filter and the sensor element. Additionally, it is preferred that the temperatures of the catalytic filter and the sensor element be known in order to establish the calibration curve for the measurement system.

A method of determining the total $NO_x$ content in a gas of the present invention comprises: (a) exposing the gas comprising $NO_x$ to a catalytic filter comprising platinum and a zeolite for a sufficient time so as to form an equilibrium mixture of NO and $NO_2$ from the gas comprising $NO_x$, (b) exposing the equilibrium mixture of NO and $NO_2$ to a sensor element comprising a sensing potentiometric electrode and a reference potentiometric electrode each disposed on an electrolyte substrate so as to obtain a potential difference between the two electrodes, and (c) determining the total $NO_x$ content in the gas comprising $NO_x$ from the potential difference via a calibration curve.

Using the present invention, the total $NO_x$ content may be determined from a gas at any temperature, including those in high temperature exhaust streams in the range of about 400° C. to about 600° C. The gas comprising $NO_x$ may additionally comprise other gases such as carbon monoxide and oxygen. It is preferred that any oxygen present be at a substantially constant concentration because the measurement system employs a calibration curve for $NO_x$ concentration determination that is oxygen sensitive. However, minor variation in the oxygen concentration will not cause substantial error.

A second method for determining the total $NO_x$ content in a gas comprising $NO_x$ of the present invention comprises: conducting the gas comprising $NO_x$ through a gas conduit having an upstream end and a downstream end. The gas conduit has disposed therein a catalytic filter comprising platinum and a zeolite. The catalytic filter catalyzes the gas to form an equilibrium mixture of NO and $NO_2$. The gas then passes over a sensor element comprising a sensing potentiometric electrode and a reference potentiometric electrode each on a solid electrolyte downstream of the catalytic filter where the potential difference between the sensing potentiometric electrode and the reference potentiometric electrode is measured. The total $NO_x$ content is then determined by comparing the potential difference with a calibration curve.

BRIEF DESCRIPTION OF THE DRAWINGS

Novel features and advantages of the present invention, in addition to those mentioned above, will become apparent to those skilled in the art from a reading of the following detailed description in conjunction with the accompanying drawings wherein similar reference characters refer to similar parts and in which.

DETAILED DESCRIPTION OF THE PREFERRED EMBODIMENT(S)

Figure 1:
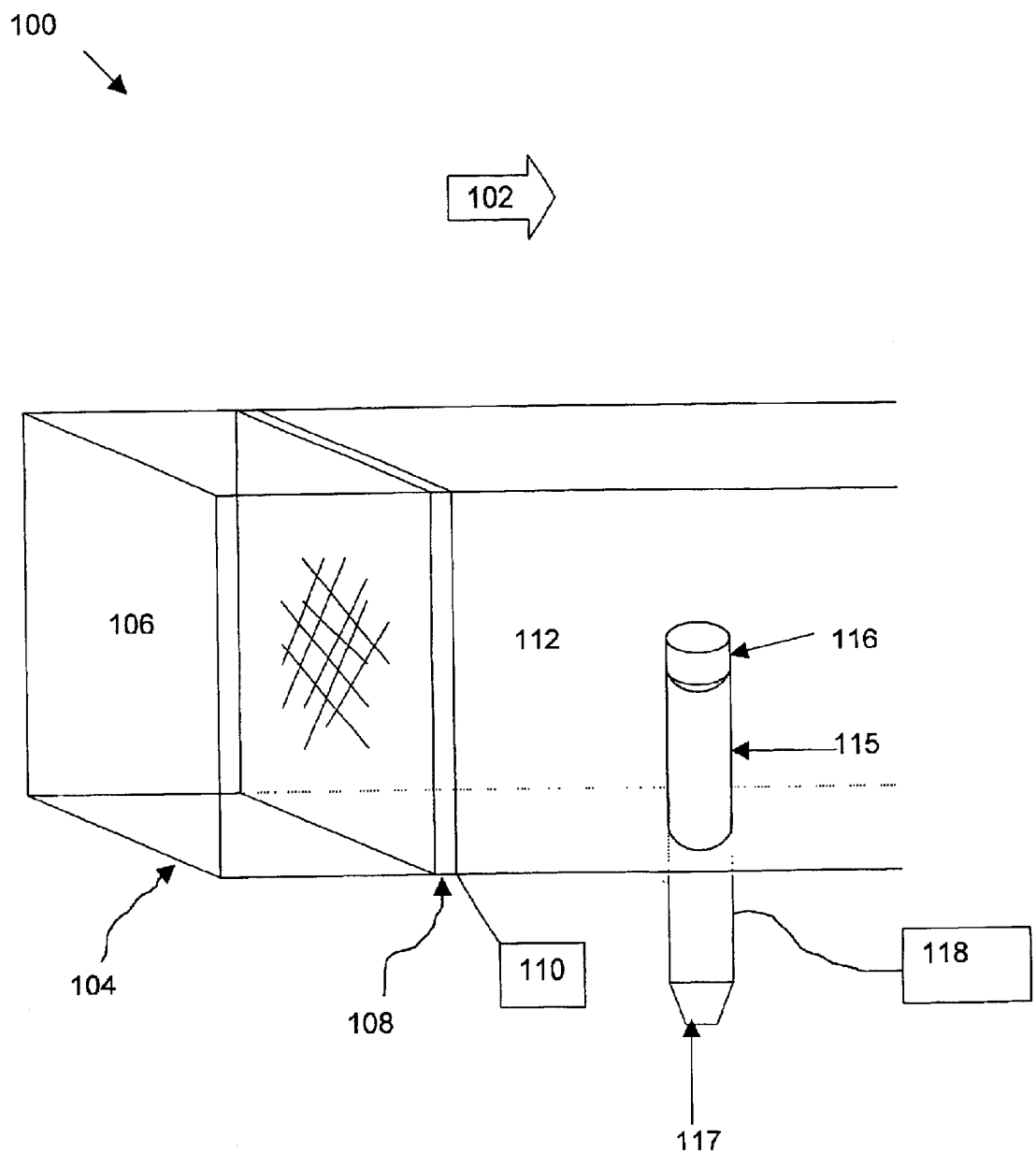
FIG. 1 illustrates a measurement system of the present invention.

As shown in FIG. 1, a preferred measurement system 100 of the present invention is presented, The measurement system 100 of FIG. 1 comprises a gas conduit 104 in which a gas comprising $NO_x$ flows. The gas flows in the direction indicated by arrow 102 such that the gas encounters catalytic filter 108 prior to contacting a sensor element comprising an YSZ substrate 115 carrying sensing potentiometric electrode 116 and reference potentiometric electrode 117. The temperature of the sensor element is maintained by heating element 118. The catalytic filter 108 comprises platinum and zeolite Y. Catalytic filter 108 is a microporous membrane whose temperature is maintained by heating element 110. In addition to maintaining the temperature of the catalytic filter and the sensor element, heating elements 110, 118 may additionally monitor and control the temperature of the device to which they are connected. For example, a heating element may supply only supplemental heat to compensate for variations in the temperature of the gas stream. Appropriate heating elements may vary from application to application but will be obvious to those of ordinary skill in the art. Catalytic filter 108 catalyzes the gas comprising $NO_x$ in region 106 such that the downstream gas in region 112 contains an equilibrium concentration of NO and $NO_2$. The potential difference between the sensing potentiometric electrode 116 in region 112 and the reference potentiometric electrode 117 referenced to air is measured. The measurement system 100 uses the potential difference to determine the total $NO_x$ content in the gas flowing through the gas conduit 104.

The gas flowing in conduit 104 may comprise any mixture of NO, $NO_2$, CO and $O_2$.

Gas Sensing Experiments

Gas sensing experiments were conducted to validate the performance of the measurement system of the present invention. The catalytic filter, sensor element and experimental apparatus used to conduct the gas sensing experiments are described below.

Catalytic Filter

The catalytic filter of the present invention is a microporous material known as platinum-zeolite Y (hereinafter PtY), a modified form of sodium-zeolite Y (hereinafter NaY). The PtY catalytic filter material is prepared by the ion-exchange method. The PtY used in the gas sensing experiments was formed by: (1) taking 1.0 g of commercially available NaY powder and drying it at 100° C. for four hours; (2) preparing a 5 mM solution of $Pt(NH_3)_4Cl_2$; (3) adding the 1.0 g of dried NaY to 100 ml of the 5 mM solution to begin the ion-exchange; (4) stirring this mixture at room temperature for 24 hours before centrifuging and washing with distilled water; (5) drying the resulting powder at 70° C. overnight before calcining at 300° C. for two hours; and (6) exposing the zeolite powder to a flow of 5% $H_2$/95% $N_2$ gas to reduce the Pt compound to Pt metal. The resulting zeolite PtY powder is dark brown in color. The zeolite used in the formation of the catalytic filter is typically referred to as zeolite Y, though other zeolites may be used.

Sensor Element

Figure 2:
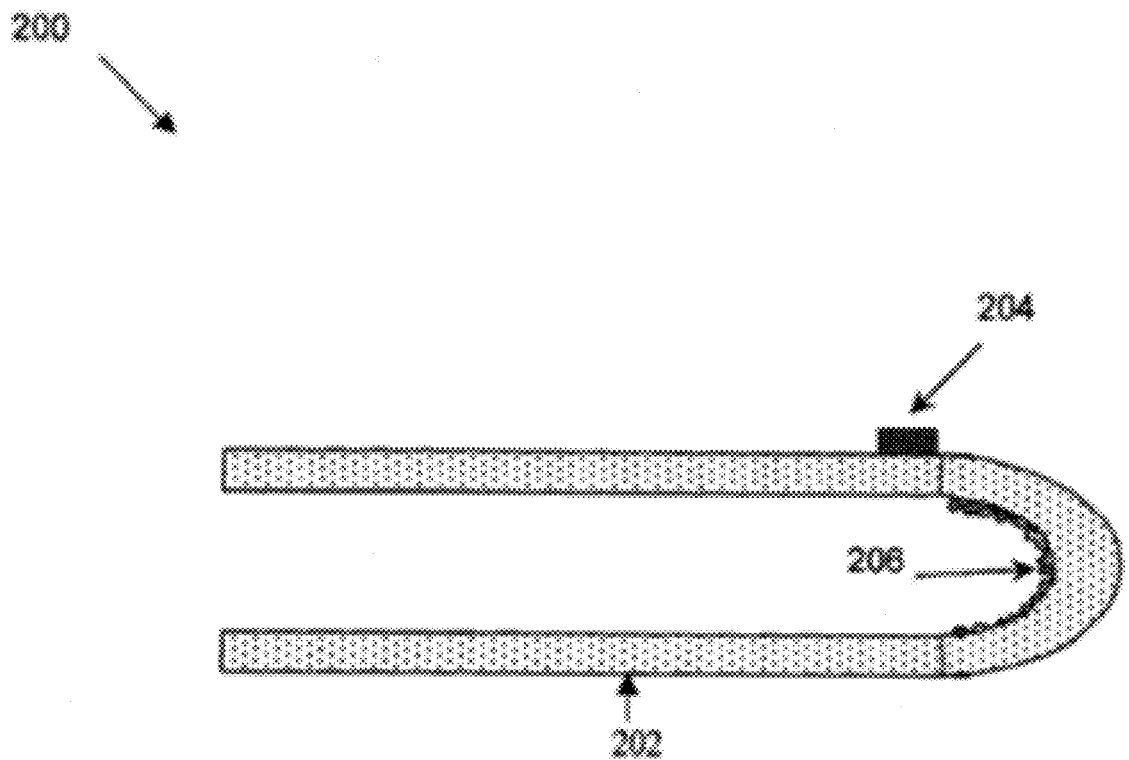
FIG. 2 shows the closed-end sensor having an air reference used in conjunction with the experimental apparatus.

With reference to FIG. 2, the sensor element 200 comprises an electrolyte substrate 202 upon which are disposed a sensing potentiometric electrode 204 and a reference potentiometric electrode 206. The electrolyte substrate 202 used in the gas sensing experiments consists of a single closed-end YSZ tube (Vesuvius McDanel, 8 mol % YSZ) approximately 305 mm in length having an inside diameter of 8 mm and a 2 mm thick wall. The reference potentiometric electrode 206 was constructed from a Pt ink (Englehard Corporation, lot #A4731) painted inside the YSZ tube. The Pt ink was subsequently cured at 1250° C. for 2 hours with a 6° C./min heating and cooling rate. The reference potentiometric electrode 206 is referenced to air. Electrical contact with the reference potentiometric electrode 206 was made by inserting a small alumina tube containing a Pt wire to make contact mechanically (not shown). The sensing potentiometric electrode 204 was constructed by first forming a paste from $Cr_2O_3$ consisting of a 50:50 mixture of the oxide and a terpineol organic solvent. A Pt wire was wrapped around the outside of the YSZ tube and the paste was painted on top of the wire in a band around the tube circumference. The paste was then cured at 750° C. for 2 hours with a 6° C./min heating and cooling rate. The sensing potentiometric electrode 204 contacts the gas to be measured.

Experimental Apparatus

Figure 3:
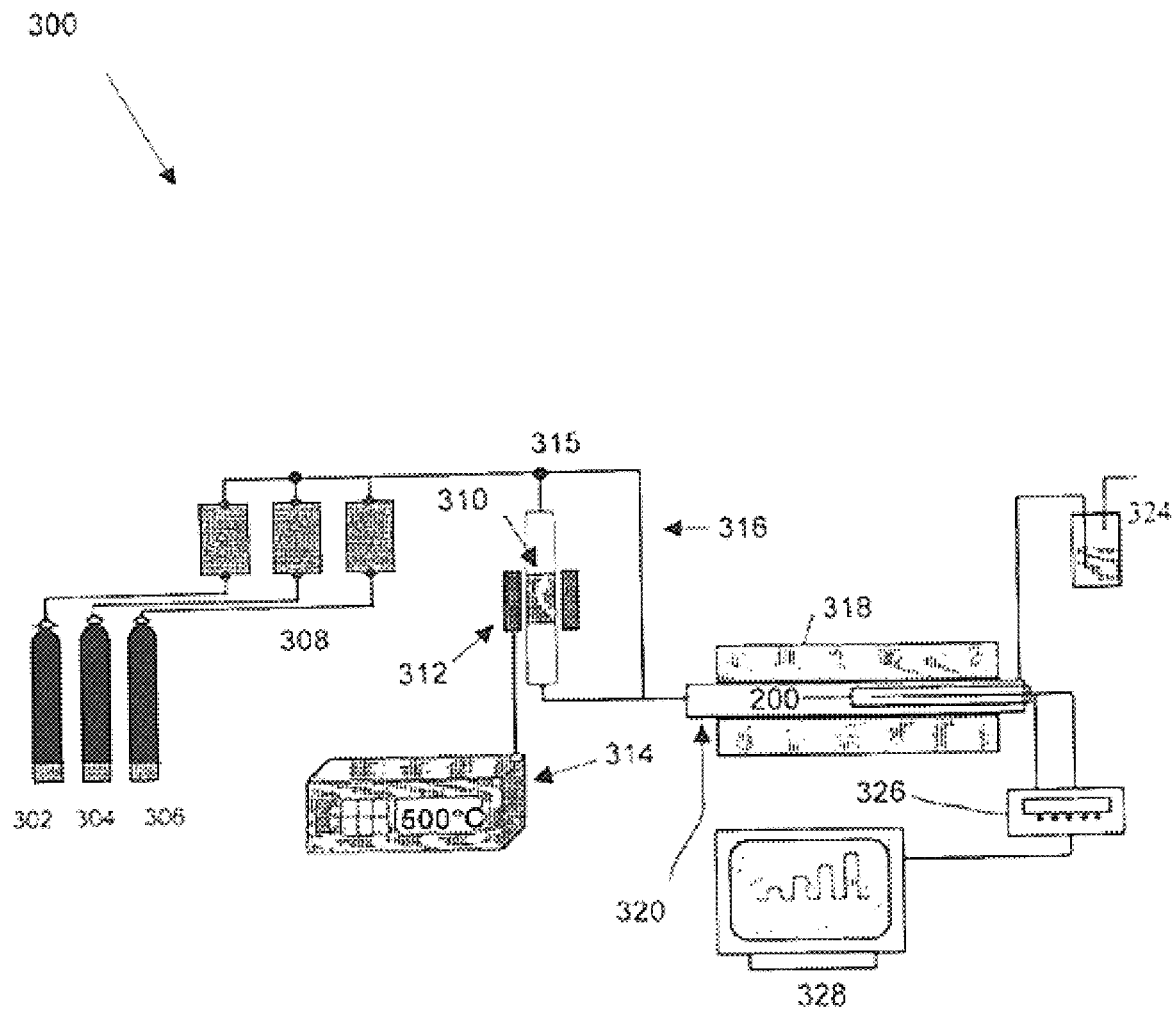
FIG. 3 is a diagram of the experimental set-up used in conjunction with the present invention.

Gas sensing experiments were conducted in an experimental apparatus shown in FIG. 3. The experimental apparatus 300 comprises a source of $N_2$ 302, a source of Air 304, and a source of nitrogen oxide (NO and/or $NO_2$) 306. Additional gas sources may be attached as required by the particular experiment. For example, a source of CO may be additionally attached to the experimental apparatus by methods known to those in the art. Each of the gas sources is connected to a mass flow meter 308 to regulate the flow of the corresponding gas. Suitable mass flow meters are produced by Sierra. After passing through the mass flow meters 308 a gas may be directed to the catalytic filter 310 or directed to the filter bypass 316 by bypass valve 315.

If bypass valve 315 is closed, the gas flows to the catalytic filter 310 located inside of heater 312. Heater control box 314 regulates the delivery of heat to the catalytic filter 310 by the heater 312. The catalytic filter 310 establishes an equilibrium mixture of NO and $NO_2$ at a temperature specified by the heater control box 314. After passing through the catalytic filter 310, the gas is directed to tube furnace 318.

However, if bypass valve 315 is open, the gas flows directly to the tube furnace 318 without first passing through the catalytic filter 310.

Tube furnace 318 is used to heat sensor element 200 at a programmed rate as well as maintaining sensor element 200 at a constant temperature (for example 500° C.). The tube furnace 318 houses a quartz tube 320. Sensor element 200 is placed inside quartz tube 320 where one electrode of sensor element 200 is exposed to the gas flowing through the tube furnace 318. The other electrode of sensor element 200 is exposed to air. The quartz tube 320 is connected by metal-to-glass fittings to a stainless steel tubing valve flow system. The gas from either the catalytic filter 310 or the filter bypass 316 flows through the quartz tube 320 where it encounters sensor element 200. After encountering sensor element 200, the gas is released from quartz tube 320 to the atmosphere by vent 324. Sensor element 200 is in electrical communication with multimeter 326. Multimeter 326 is a Hewlett Packard data acquisition unit (model 34970A) that monitors the voltage outputs of the sensor element's electrodes' response to changes in the gas concentrations. Multimeter 326 is in electrical communication with computer 328 running Hewlett Packard Benchlink software to record the data sent by multimeter 326.

The Experiments and Their Results

Figure 4:
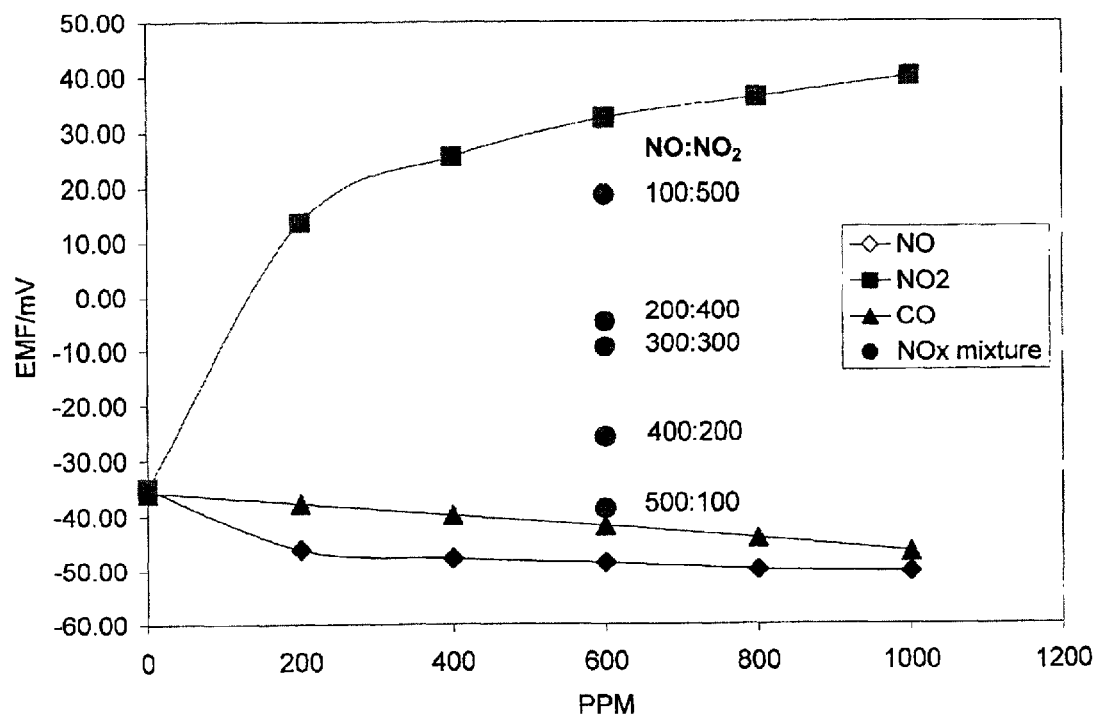
FIG. 4 is a sensitivity plot for NO, $NO_2$, CO and total $NO_x$ mixtures at 600 ppm.

Using the experimental apparatus 300 described above and 80 mg of the catalytic filter 310, the sensor element 200 was heated to 500° C. under a flow of a background gas of 3% $O_2$ and 97% $N_2$. The sensing behavior towards NO and $NO_2$ were investigated separately in the range of 0–1000 ppm. FIG. 4 shows the sensitivity plot of both the NO and $NO_2$ response of the electrode from 0–1000 ppm. FIG. 4 shows that the response to NO is In the opposite direction of the response to $NO_2$, as is typical of mixed potential type sensors.

A complete range of mixtures at a total $NO_X$ of 600 ppm was tested. The mixture ratio started at 600 ppm NO, changing to 600 ppm $NO_2$ in 100-ppm increments while keeping the total $NO_X$ at 600 ppm. FIG. 4 also shows the results of these tests. When both species are present, the response is different than that obtained with either pure NO or pure $NO_2$. The results show that as more $NO_2$ is added, that the signal migrates closer to the 600 ppm $NO_2$ signal. Similarly, as more NO is added, the signal gets closer to the 600 ppm NO signal. This indicates that it is difficult to make a sensor for the determination of total $NO_X$ species when the electrode responds to both gases. This has been an ongoing challenge to the development of a practical sensor for $NO_X$.

An important interfering gas is CO, which can show significant interference on mixed potential electrodes. FIG. 4 shows the sensitivity plot of a $Cr_2O_3$ electrode exposed to CO in the range of 0–1000 ppm. From FIG. 4, it is clear that the presence of CO in the sensed gas would contribute to the total signal, thereby causing error in the determination of total $NO_X$. Thus, the elimination of CO from the sensed gas would be beneficial in the determination of total $NO_X$.

One way to eliminate the interference effect of the CO is to use a catalytic filter 310. A zeolite material was investigated for its ability to convert CO to $CO_2$ because $CO_2$ has no effect on the sensor. Catalytic filter 310 therefore serves two purposes: first the catalytic filter 310 eliminates the interference effect of any CO present in the gas stream; and second, the catalytic filter 310 equilibrates the incoming $NO_X$ to a fixed ratio of NO and $NO_2$ depending upon the temperature and oxygen concentration of the gas stream. A preferred catalytic filter 310 for converting CO to $CO_2$ is PtY. The ability of PtY to convert CO to $CO_2$ was confirmed by gas chromatography.

Figure 5:
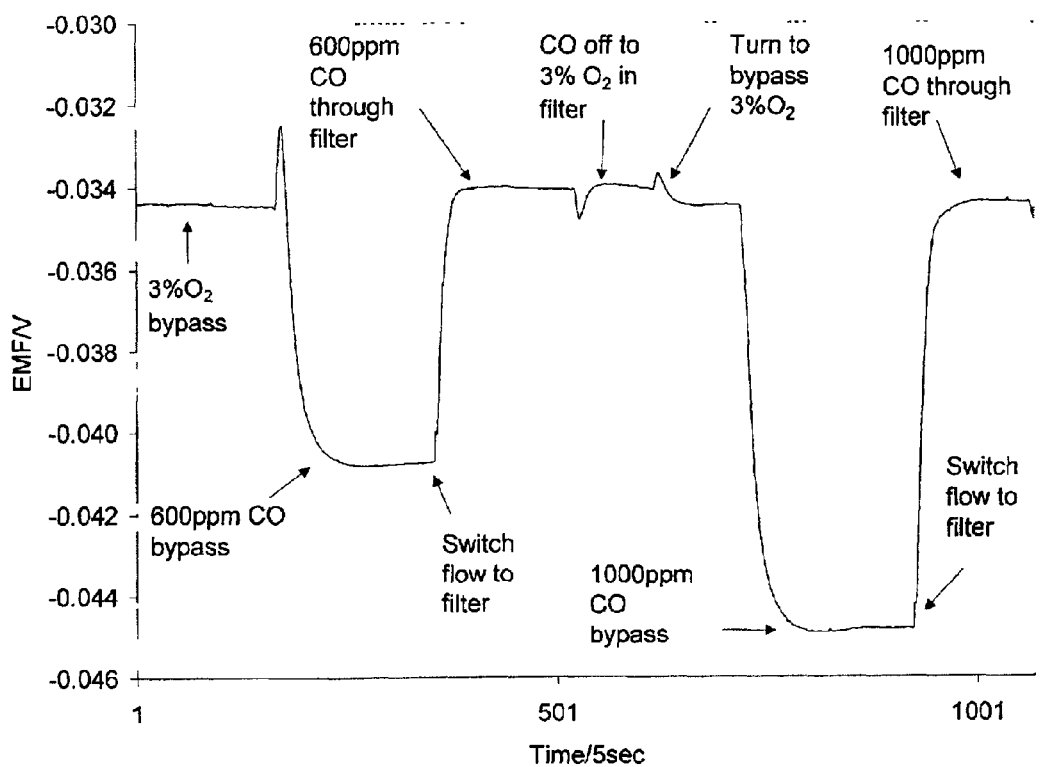
FIG. 5 demonstrates capabilities of the PtY filter for 600 and 1000 ppm of CO.

To determine the filtering ability of the PtY catalytic filter 310, a flow of 600 ppm of CO was directed through filter bypass 316. FIG. 5 shows the change in EMF from the baseline caused by 600 ppm CO in the absence of the catalytic filter 310. During this experiment, a data point was collected approximately every 5 seconds. The flow of CO was then diverted to catalytic filter 310. The catalytic filter 310 completely removes the interference of CO as shown from the transient plot in FIG. 5. In the experimental results illustrated by FIG. 5, sensor element 200 was additionally exposed to 1000 ppm of CO. Again, the CO was first sent to sensor element 200 via filter bypass 316 and a change in EMF from the baseline was observed. Then the CO flow was directed to the catalytic filter 310 and again we observed that the catalytic filter 310 removes the interference of CO. It can be seen that even at 1000 ppm CO, the CO is totally removed when the gas flows through the catalytic filter 310. This is important because in industrial applications, CO may be present in some amount at the same time as $NO_x$.

Figure 6:
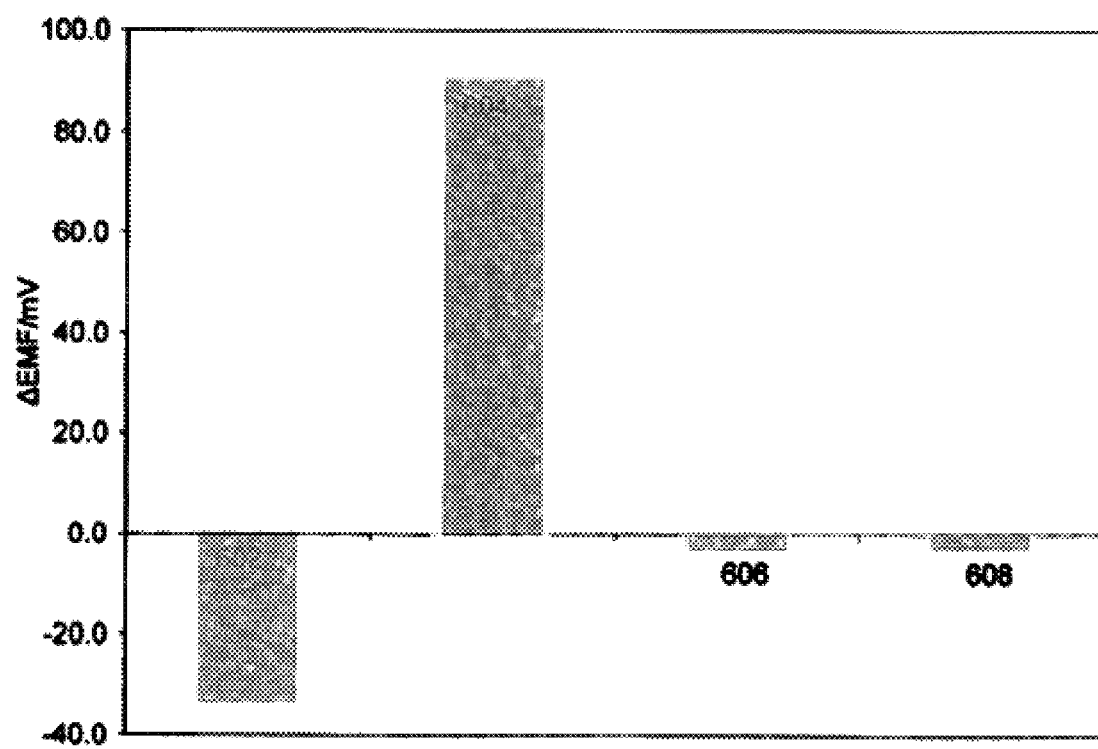
FIG. 6 is a histogram for $NO_x$ and CO response.

The catalytic filter 310 was then tested for its ability to equilibrate $NO_x$. FIG. 6 shows a histogram for sensor element absolute response at 500° C. without the catalytic filter for 1000 ppm NO 602 and 1000 ppm $NO_2$ 604. Additionally, FIG. 6 shows the sensor element response at 500° C. with the catalytic filter for 1000 ppm NO 606 and 1000 ppm $NO_2$ 608. It is observed that after passing through the catalytic filter both NO and $NO_2$ yield the same signal. However, the signal is small because of a negligible difference in temperature between the catalytic filter 310 and the sensor element 200.

Figure 7:
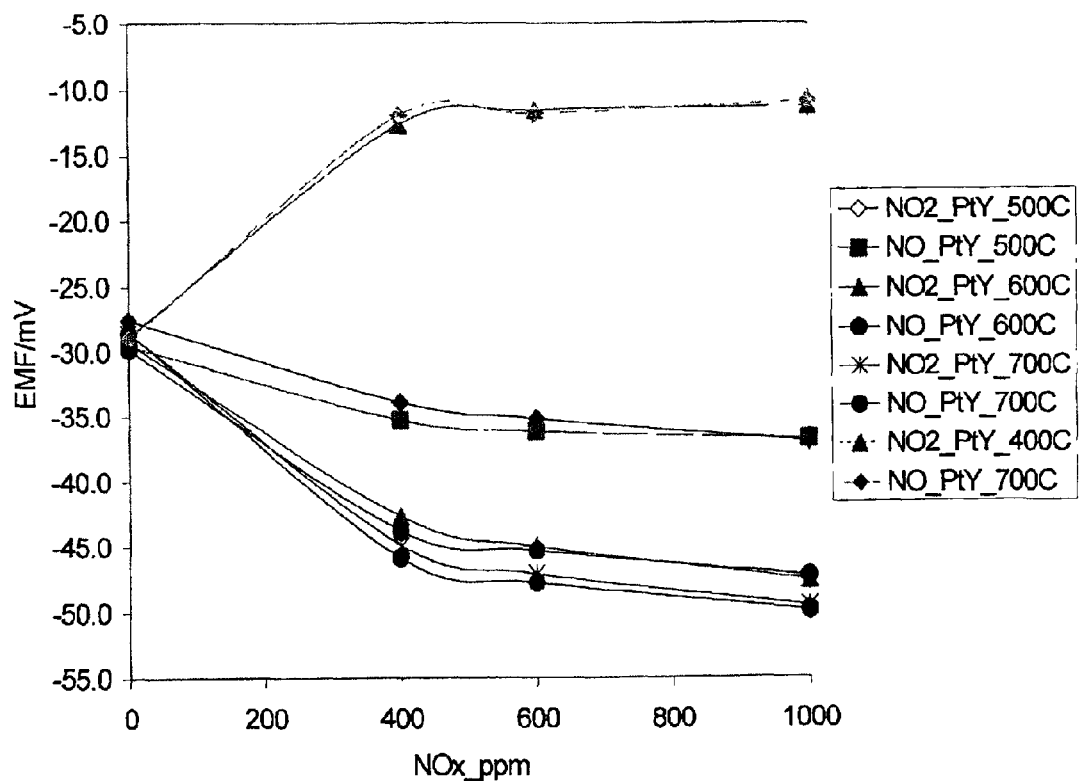
FIG. 7 shows the sensor response at 500° C. when the catalytic bed is varied from 400 to 700° C.

To increase the signal to total $NO_x$ the catalytic filter 310 was varied in temperature from 400–700° C. while sensor element 200 was kept at 500° C. FIG. 7 shows that when NO or $NO_2$ passes through the catalytic filter that an equilibrium mixture is formed, as indicated by the similarity of response curves. FIG. 7 also shows that a temperature difference between the catalytic sensor 310 and sensor element 200 is required to produce a large change in EMF upon $NO_x$ exposure. Thus, the magnitude of the signal is increased when the absolute difference in temperature between catalytic filter 310 and sensor element 200 is increased.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims, which are incorporated herein by reference.

REFERENCES

1. S. Zhuiykov, M. Muta, T. Ono, M. Hasei, N. Yamazoe, N. Miura,"Stabilized Zirconia-Based $NO_x$ Sensor Using $ZnFe_2O_4$ Sensing Electrode," *Electrochemical and Solid State Letters*, 4, No.9, H19–H21, (2001).
2. B. Ruhland, Th. Becker, G. Müeller, "Gas-Kinetic Interactions of Nitrous Oxides with $SnO_2$ Surfaces," *Sensors and Actuators B*, 50, pp. 85–94 (1998).
3. N. Imanaka, Y. Hirota, G. Adachi, "Nitrogen Oxides Sensor Based on Silicon Nitride Refractory Ceramics," *Electrochemical Society and Solid-State Leffers*, 2, No. 2, pp. 100–101, (1999).
4. H. Kurosawa, Y. Yan, N. Miura, N. Yamazoe, "Stabilized Zirconia-Based $NO_x$ Sensor Operative at High Temperature," *Solid State Ionics*, 79, pp. 338–343 (1995).
5. S. Zhuiykov, T. Nakano, A. Kunimoto, N. Yamazoe, N. Miura,"Potentiometric $NO_x$ Sensor Based on Stabilized Zirconia and $NiCr_2O_4$ Sensing Electrode Operating at High Temperatures," *Electrochemistry Communications*, 3, pp. 97–101, (2001).
6. N. Miura, G. Lu, M. Ono, N. Yamazoe, "Selective Detection of NO by Using an Amperometric Sensor Based on Stabilized Zirconia and Oxide Electrode," *Solid State Ionics*, 117, pp. 283–290 (1999).
7. N. Miura, G. Lu, N. Yamazoe, "High-Temperature Potentiometric/Amperometric $NO_x$ Sensors Combining Stabilized Zirconia with Mixed-Metal Oxide Electrode," *Sensors and Actuators B*, vol. 52, pp. 169–178 (1998).
8. G. Sberveglieri, S. Gropellia, P. Nelli, V. Lantto, H. Torvela, P. Romppainen, S. Leeppävuori, "Response to Nitric Oxide of Thin and Thick $SnO_2$ Films Containing Trivalent Additives," *Sensors and Actuators B*1, pp. 79–82 (1990).
9. C. Baratto, G. Sberveglieri, E. Comini, G. Faglia, G. Benussi, V. La Ferrara, L. Quercia, G. Di Francia, V. Guidi, D. Vincenzi, D. Boscarino, V. Rigato, "Gold-Catalyzed Porous Silicon for $NO_x$ Sensing," *Sensors and Actuators B*, vol. 68, pp. 74–80, (2000).
10. B. Fruhberger, N. Stirling, F. G. Grillo, S. Ma, D. Ruthven, R. J. Lad, B. G. Frederick, "Detection and Quantification of Nitric Oxide in Human Breath Using a Semiconducting Oxide Based Chemiresistive Microsensor," *Sensors and Actuators B*, vol. 76, pp. 226–234 (2001).
11. M. Ono, K. Shimanoe, N. Miura, N. Yamazoe, "Amperometric Sensor Based on NASICON and NO Oxidation Catalysts for Detection of Total $NO_x$ in Atmospheric Environment," *Solid State Ionics*, vol. 136–137, pp. 583–588, (2000).
12. T. Takahashi, N. Ogawa, T. Yoshida, Y. Katsuda, "$NO_x$ Sensor", U.S. Pat. No. 5,705,129A, (1998).
13. M. Fleischer, S. Komely, T. Weh, J. Frank, H. Meixner, "Selective Gas Detection with High-temperature Operated Metal Oxides Using Catalytic Filters," *Sensors and Actuators B*, vol. 69, pp. 205–210 (2000).
14. S. Kitsukawa, H. Nakagawa, K. Fukuda, S. Asakura, S. Takahashi, T. Shigemori, "The Interference Elimination for Gas Sensor by Catalyst Filters," *Sensors and Actuators B*, vol. 65, pp. 120–121 (2000).
15. K. Fukui, S. Nishida, "CO Gas Sensor Based on $Au-La_2O_3$ Added $SnO_2$ Ceramics With Siliceous Zeolite Coat," *Sensors and Acutators B*, vol. 45, pp. 101–106, (1997).
16. O. Hugon, M. Sauvan, P. Benech, C. Pijolat, F. Lefebvre, "Gas Separation With a Zeolite Filter, Application to the Selectivity Enhancement of Chemical Sensors," *Sensors and Actuators B*, vol. 67, pp. 235–243, (2000).
17. K. Kaneyasu, K. Otsuka, Y. Setoguchi, S. Sonoda, T. Nakahara, I. Aso, N. Nakagaichi, "A Carbon Dioxide Gas Sensor Based on Solid Electrolyte for Air Quality Control," *Sensors and Actuators B*, vol. 66, pp. 56–58, (2000).
18. N. F. Szabo, H. Du, S. A. Akbar, A. Soliman, P. K. Dutta, "Microporous Zeolite Modified Yttria Stabilized Zirconia (YSZ) Sensors for Nitric Oxide (NO) Determination in Harsh Environments," *Sensors and Actuators B*, in press (2002).

The aforementioned references are hereby incorporated herein by reference.

What is claimed is:

1. A measurement system for determining total $NO_x$, including NO and $NO_2$ concentration from a gas comprising:
   a gas conduit having an upstream end and a downstream end, said gas conduit adapted to carry a gas comprising $NO_x$;
   a catalytic filter disposed so as to contact said gas comprising $NO_x$ in said gas conduit, said catalytic filter comprising a zeolite PtY, said catalytic filter adapted to catalyze the formation of an equilibrium mixture of NO and $NO_2$ from said gas comprising $NO_x$; and
   a sensor element, said sensor element comprising an electrolyte substrate upon which are disposed a sensing potentiometric electrode and a reference potentiometric electrode, said sensing potentiometric electrode adapted to contact said equilibrium mixture of NO and $NO_2$, wherein said catalytic filter and said sensor element are at different temperatures.

2. A measurement system according to claim 1 wherein said gas comprising $NO_X$ additionally comprises carbon monoxide.

3. A measurement system according to claim 1 wherein said gas comprising $NO_X$ additionally comprises oxygen.

4. A measurement system according to claim 1 wherein said electrolyte substrate is yttria stabilized zirconia.

5. A measurement system according to claim 1 wherein said reference potentiometric electrode is referenced to air.

6. A measurement system according to claim 1 wherein said catalytic filter is maintained at a temperature below approximately 700° C.

7. A measurement system according to claim 1 wherein said sensor element is maintained at a temperature above approximately 400° C. and below approximately 600° C.

8. A measurement system for determining total $NO_X$, including NO and $NO_2$ concentration, from a gas stream comprising:
a catalytic filter, said catalytic filter adapted to be placed in a conduit in which a gas stream containing $NO_X$ is flowing, said catalytic filter adapted to contact said gas stream, said catalytic filter comprising a zeolite PtY, wherein said catalytic filter forms an equilibrium mixture of NO and $NO_2$ from said gas stream; and
a sensor element comprising an electrolyte substrate upon which are disposed a sensing potentiometric electrode and a reference potentiometric electrode, said sensing potentiometric electrode disposed so as to contact said gas stream after said formation of said equilibrium mixture of NO and $NO_2$, said reference potentiometric electrode referenced to air, said sensing potentiometric electrode in comparative electrical contact with said reference potentiometric electrode.

9. A measurement system according to claim 8, wherein said gas stream additionally comprises carbon monoxide.

10. A measurement system according to claim 8, wherein said gas stream additionally comprises oxygen.

11. A measurement system according to claim 8, wherein said catalytic filter and said sensor element are each maintained at a different temperature.

12. A measurement system according to claim 8 wherein said electrolyte substrate is yttria stabilized zirconia.

13. A method of determining the total $NO_X$ content in a gas comprising $NO_X$ comprising:
exposing said gas comprising $NO_X$ to a catalytic filter comprising a zeolite PtY so as to form an equilibrium mixture of NO and $NO_2$ from said gas comprising $NO_X$;
exposing said equilibrium mixture of NO and $NO_2$ to a sensor element, said sensor element comprising an electrolyte substrate upon which are disposed a sensing potentiometric electrode and a reference potentiometric electrode, wherein said sensing potentiometric electrode is in comparative electrical communication with said reference potentiometric electrode, said sensing potentiometric electrode and said reference potentiometric electrode adapted to obtain a potential difference therebetween; and
determining the total $NO_X$ content in said gas comprising $NO_X$ by comparing said potential difference with a calibration curve.

14. A method according to claim 13 wherein said total $NO_X$ content is determined from said gas comprising $NO_X$ while said gas comprising $NO_X$ is at a temperature in the range of about 400° C. to about 600° C.

15. A method according to claim 13 wherein said gas comprising $NO_X$ additionally comprises carbon monoxide.

16. A method according to claim 13 wherein said gas additionally comprises oxygen.

17. A method according to claim 13 wherein said catalytic filter is maintained at a different temperature than said sensor element.

18. A method for determining the total $NO_X$ content in a gas comprising $NO_X$, said method comprising:
conducting said gas comprising $NO_X$ through a gas conduit having an upstream end and a downstream end, said gas conduit containing:
a catalytic filter, said catalytic filter comprising a zeolite PtY, said catalytic filter adapted to form an equilibrium mixture of NO and $NO_2$ from said gas comprising $NO_X$; and
a sensor element, said sensor element comprising an electrolyte substrate upon which are disposed a sensing potentiometric electrode and a reference potentiometric electrode, said sensing potentiometric electrode disposed downstream of said catalytic filter so as to contact said equilibrium mixture of NO and $NO_2$, said sensing potentiometric electrode in comparative electrical contact with said reference potentiometric electrode, wherein said catalytic filter and said sensor element are each maintained at different temperatures; and
obtaining a potential difference between said sensing potentiometric electrode and said reference potentiometric electrode; and
determining the total $NO_X$ content in said gas comprising $NO_X$ by comparing said potential difference with a calibration curve.

19. A method according to claim 18 wherein said total $NO_X$ content is determined from said gas comprising $NO_X$ while said gas comprising $NO_X$ is at a temperature in excess of about 500° C.

20. A method according to claim 18 wherein said gas comprising $NO_X$ additionally comprises carbon monoxide.

21. A method according to claim 18 wherein said gas comprising $NO_X$ additionally comprises oxygen at a substantially constant concentration.

* * * * *

UNITED STATES PATENT AND TRADEMARK OFFICE
CERTIFICATE OF CORRECTION

PATENT NO. : 6,764,591 B1
DATED : July 20, 2004
INVENTOR(S) : Dutta et al.

It is certified that error appears in the above-identified patent and that said Letters Patent is hereby corrected as shown below:

Title page,
Item [56], References Cited, OTHER PUBLICATIONS, please delete
"Osada, M. et al., Synthesis of a Faujasite Thin Layer and its Application for SO2 Sensing at Elevated Temperatures, Microporous and Mesoporous Materials, 23, pp. 287-294 (1998). " and insert -- Osada, M. et al., Synthesis of a Faujasite Thin Layer and its Application for SO2 Sensing at Elevated Temperatures, Microporous and Mesoporous Materials, 23, pp. 287-294 (1998). --.
Please delete "Liu, B., et al., A Reagentless Amperometric Biosensor Based on the Coimmobilization of Horseradish Peroidase and Methylene Green in a Modified zeolite Matrix, Analytica Chimica Acta, 386, pp. 31-39 (1999)." and insert -- Liu, B., et al., A Reagentless Amperometric Biosensor Based on the Coimmobilization of Horseradish Peroidase and Methylene Green in a Modified Zeolite Matrix, Analytica Chimica Acta, 386, pp. 31-39 (1999). --.
Please delete "Kunzellman, U. et al., Biosensor Properties of Glucose Oxidase Immobilized Within SiO2Gels, Sensors and Actuators B, 39, pp. 222-228 (1997)." and insert -- Kunzellman, U. et al., Biosensor Properties of Glucose Oxidase Immobilized within SiO2 Gels, Sensors and Actuators B, 39, pp. 222-228 (1997). --.
Please delete "Simon, U. et al., The effect of NH3on the Ionic Conductivity of Dehydrated Zeolites Nabeta and Ubeta, Microporous and Mesoporous Materials, 21, pp. 111-116 1998." and insert -- Simon, U. et al., The effect of NH3 on the Ionic Conductivity of Dehydrated Zeolites Nabeta and Hbeta, Microporous and Mesoporous Materials, 21, pp. 111-116 1998. --.

Column 2,
Line 4, please delete "150° C." and insert -- 150°C --.
Line 63, please delete "700° C." and insert -- 700°C --.

Column 3,
Lines 8-9, please delete "400° C." and insert -- 400°C --.
Line 15, please delete "100° C." and insert -- 100°C --.
Lines 35-36, please delete "400° C." and insert -- 400°C --.

UNITED STATES PATENT AND TRADEMARK OFFICE
CERTIFICATE OF CORRECTION

PATENT NO. : 6,764,591 B1
DATED : July 20, 2004
INVENTOR(S) : Dutta et al.

It is certified that error appears in the above-identified patent and that said Letters Patent is hereby corrected as shown below:

Column 4,
Line 13, please delete "500° C." and insert -- 500°C --.
Line 20, please delete "presented," and insert -- presented. --.
Line 65, please delete "100° C." and insert -- 100°C --.

Column 5,
Line 4, please delete "70° C." and insert -- 70°C --.
Line 4, please delete "300° C." and insert -- 300°C --.
Line 21, please delete "1250° C." and insert -- 1250°C --.
Line 22, please delete "6° C./min" and insert -- 6°C/min --.
Line 32, please delete "750° C." and insert -- 750°C --.
Line 33, please delete "6° C./min" and insert -- 6°C/min --.
Line 63, please delete "500° C." and insert -- 500°C --.

Column 6,
Line 18, please delete "500° C." and insert -- 500°C --.
Line 23, please delete "In" and insert -- in --.

Column 7,
Line 13, please delete "500° C." and insert -- 500°C --.
Line 16, please delete "500° C." and insert -- 500°C --.
Line 23, please delete "400-700° C." and insert -- 400-700°C --.
Line 53, please delete "Lefers" and insert -- Letters --.

Column 8,
Line 26, please delete "S. Komely" and insert -- S. Kornely --.
Line 27, please delete "High-temperature" and insert - High-Temperature --.

UNITED STATES PATENT AND TRADEMARK OFFICE
CERTIFICATE OF CORRECTION

PATENT NO.    : 6,764,591 B1
DATED         : July 20, 2004
INVENTOR(S)   : Dutta et al.

It is certified that error appears in the above-identified patent and that said Letters Patent is hereby corrected as shown below:

Column 9,
Line 20, please delete "400° C." and insert -- 400°C --.

Column 10,
Line 13, please delete "400° C." and insert -- 400°C --.

Signed and Sealed this

Seventh Day of December, 2004

JON W. DUDAS
*Director of the United States Patent and Trademark Office*